United States Patent [19]

Marcina et al.

[11] Patent Number: 4,652,395

[45] Date of Patent: Mar. 24, 1987

[54] TAGGANT COMPOSITION

[75] Inventors: George L. Marcina, Huntington Beach; Francis E. Lawlor, Carson; Paul H. Beemer, Whittier; Lawrence A. Balling, Woodland Hills, all of Calif.

[73] Assignee: The W. W. Henry Company, Huntington Park, Calif.

[21] Appl. No.: 789,319

[22] Filed: Oct. 21, 1985

[51] Int. Cl.[4] .............................................. C09K 11/06
[52] U.S. Cl. ........................ 252/301.35; 250/462.1; 252/301.16; 252/301.34; 252/301.36; 427/157
[58] Field of Search ....................... 252/301.35, 301.34, 252/301.36, 301.16

[56] References Cited

U.S. PATENT DOCUMENTS

| | | | |
|---|---|---|---|
| 2,247,259 | 6/1941 | Snell | 252/301.16 |
| 2,392,620 | 1/1946 | Sparks | 252/301.36 |
| 2,498,592 | 2/1950 | Switzer | 252/301.35 |
| 2,620,311 | 12/1952 | Bleecker | 252/301.16 |
| 2,631,243 | 3/1953 | Weber et al. | 252/301.35 |
| 2,938,873 | 5/1960 | Kazenas | 252/301.35 |
| 3,361,677 | 1/1968 | Voedisch | 252/301.35 |
| 3,642,650 | 2/1972 | McIntosh | 252/301.35 |
| 3,812,054 | 5/1974 | Noetzel et al. | 252/301.35 |
| 3,856,550 | 12/1974 | Bens et al. | 252/301.35 |
| 4,238,384 | 12/1980 | Blumberg | 250/302 |

FOREIGN PATENT DOCUMENTS

| | | | |
|---|---|---|---|
| 753371 | 5/1966 | Canada | 252/301.34 |
| 1029512 | 5/1966 | United Kingdom | 252/301.35 |

Primary Examiner—Arthur P. Demers
Attorney, Agent, or Firm—Marvin E. Jacobs

[57] ABSTRACT

Resin based, film-forming compositions such as adhesives are coded for identification by dispersing insoluble fluorescent taggant particles within the resin phase of the composition. The taggant is readily identifiable even after long term storage or service on a floor or wall by peeling away the floor covering such as carpet and examining a sample of the layer of adhesive under fluorescent light to determine the pattern size and color of the taggant particles. If the particles are not readily visible, the sample can be scraped with a sharp instrument such as a putty knife to expose the taggants. If the particles are still not visible, the sample is dissolved in a heavy solvent for the resin binder and the taggant particles will often float to the top where they can be observed for size and color. Failing this, the solution and residue can be separated by filltration whereby the taggants are easily detected.

23 Claims, 2 Drawing Figures

TAGGANT COMPOSITION

TECHNICAL FIELD

The present invention relates to film forming compositions containing a visual marker and, more particularly, to resin-based adhesive, sealing or coating compositions containing a dispersion of specific fluorescent taggant particles within a film or layer of resin.

Resin-based film forming compositions find many uses in the construction industry such as roofing cements, roof coatings, floor covering adhesives, panel and subfloor construction adhesives, tile adhesives, drywall adhesives, sealants, grouts, paints, etc. Adhesives are finding more acceptance and use in construction for a variety of purposes. There is an increasing amount of litigation resulting from dissatisfaction with some aspect of a completed construction project.

Due to expanded theories of product liability and prevalence of insurance, trial lawyers tend to name all possible parties connected with a project having financial ability to respond. Many times there is no basis for being named in a lawsuit and it is expensive to defend. Many times the named defendant is caught in a situation where they must settle due to size of the financial exposure and pressure of their insurance carrier because they cannot prove they were not involved. This perverts the legal system where defendant must prove non-involvement and plaintiff wins even though he does not carry his burden to prove the liability of a particular defendant by a preponderance of the evidence.

This situation is prevalent in the construction industry. Many times there is an apparent defect in construction, such as sealant that does not set or stick, panels or tiles that do not adhere, etc. Many times the fault lies with the installer and not with the supplier or the manufacturer of the adhesive, sealant, coating composition and the like. Furthermore, many times the plaintiff and his lawyer cannot trace the supplier of the material and guess at the identity of the supplier. Though forensic chemistry has advanced substantially, it is sometimes very difficult to identify to an absolute certainty that a specific material is supplied from a particular source, especially when the material is a few years old and is a fragment from an installation and is mixed with carpet or tile fiber or residue from the wood or cement substrate.

It has been proposed to add extraneous tag compounds to construction materials that can be analyzed to a certainty. Many tag compounds are soluble in one or another component of the material and would lose their visual distinctiveness on storage. Other tag materials are reactive with a component of the construction material such as metal glitter in an alkaline base adhesive. Again distinctiveness is lost on storage. If the colorant is insoluble it may also be difficult to disperse because of incompatability with the resin matrix. Another problem is that many of the materials are opaque and the tag is obliterated. Furthermore, certain products acquire a subjective quality from their color such as white latex adhesive. Any tinting of this product would affect its marketability.

Early attempts to disperse an insoluble, fluorescent colorant in a white, opaque adhesive were technically successful, but proved to be impractical at the production level. These involved the use of wax as the matrix for 3 percent of Day-Glow Z-14 pigment. The pigmented wax was made into a coarse aqueous dispersion which was then incorporated into latex adhesive. No practical method was found, however, to control the particle size in the preparation of the dispersion. Frequently it occurred that most particles were too fine and were not readily discernible in the adhesive film.

Lustrous metal pigments such as metal glitter were also added to adhesives as a visual marker but the particles lost luster when compounded into the adhesive due to reaction with the alkaline base of the adhesive. These materials are not capable of providing an identification of source to a reasonable certainty.

STATEMENT OF THE INVENTION

A system for identifying the source of a resin-based composition to a reasonable certainty is provided by the invention. The resin-based composition is coded with a dispersion of an insoluble fluorescent taggant that has a reasonable certainty of recognition even after long-term storage in a container and/or after long-term service as a layer on a substrate.

When there is a need to identify the source of the composition, the layer is exposed, such as by tearing up carpet or floor tile, and a sample of the layer is examined under fluorescent light to determine the pattern, size and color of the taggant particles. If the particles are not readily visible, the sample can be scraped with a sharp instrument such as a putty knife to expose the taggants. If the particles are still not visible, the sample is dissolved in a heavy solvent for the resin binder and the taggant particles will often float to the top where they can be observed for size and color. Failing this, the solution and residue can be separated by filtration whereby the taggants are easily detected. The density of the solvent when filtration is used is of no importance.

The source coding material is an insoluble fluorescent pigment having a controlled size below 35 mesh to fines. The insoluble pigment is preferably a high density polyethylene having a melt index above 0.94. The pigment is prepared by compounding commercial polyethylene and 1 to 5 percent by weight of a fluorescent dye in a mixer, extruding the mixture into beads, grinding the beads to particles and screening the particles to $-35$ mesh. Fines below 325 mesh should be less than 20 percent since it is difficult to observe very fine particles in binder resin, especially when the resin contains mineral filler.

The taggants of the invention have been dispersed in aqueous, solvent or emulsion based resin compositions and applied to substrates. In each case the pattern, color and size of the dispersed taggants have been observed to specifically identify the compositions.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
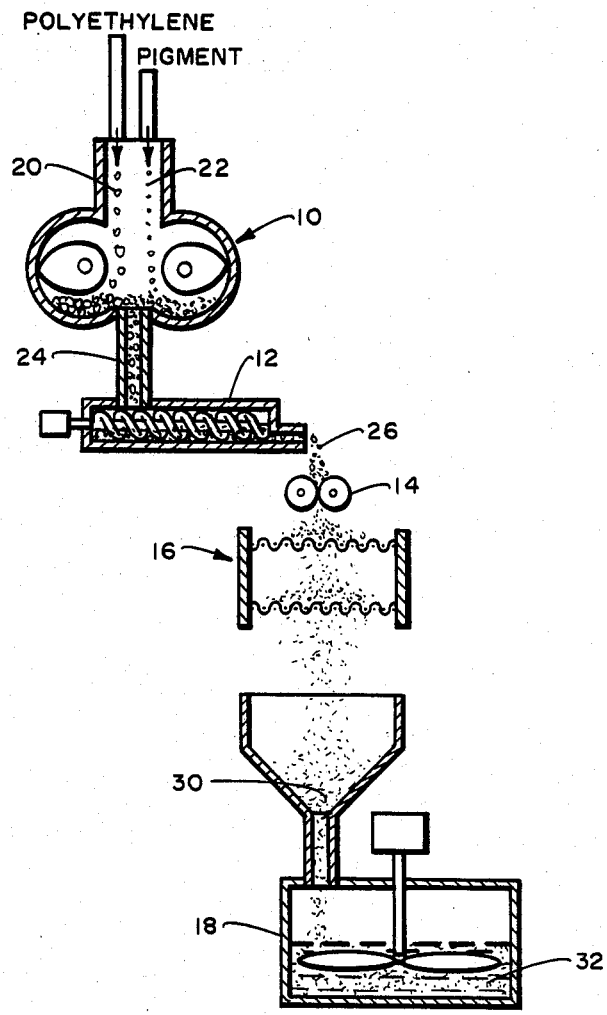
FIG. 1 is a schematic view of an apparatus for preparing the taggant particles and coded composition according to the invention.

The taggant particles are prepared by dying a substrate such as a hard particle insoluble in the resin-based adhesive or coating composition. The particle can be a thermoplastic or thermosetting plastic. It is preferably a clear, transparent material so that the dye is not masked. The plastic must be capable of being ground to a small, controlled particle size. Suitable resins are polyolefins such as polyethylene or polypropylene, preferably a hard polyethylene having a melt index above about 0.94.

The fluorescent dye can be a single dye or a mixture of dyes. If maximum fluorescence is not critical, the second dye can be a non-fluorescent dye. Several particles can be dyed with different dyes. When the particles are combined in different proportions, a whole range of specific codes are provided. For example, with four batches of differently colored beads, five possibilities are provided since absence of a single color is in itself a code. The four color beads provide fifteen easily recognized color codes, without resorting to quantitative considerations. In other words, a specimen found to contain only colors 2 and 3 would be recognized without any need to determine the proportions of the two. A far higher number of codes could be available if varied proportions were utilized and appropriate methods of examination were employed.

Certain substances, especially a number of organic dyes, have the property of fluorescing under ultraviolet light and visible light at the blue end of the spectrum. The fluorescence of these organic dyes is associated with the individual dye molecules; and in order for them to fluoresce efficiently, they must be dissolved in fairly low concentrations in a solvent for the dyes. Due to the nature of the dyes used, it is necessary to have an organic medium or carrier to put them into solution; and in order to have a pigment, it is necessary that this medium be a solid. The type of material which meets these requirements for a carrier of matrix for the dyes is an organic resin. The fluorescent pigments are transparent organic resin particles containing dyes which are capable of fluorescing while in a solid state solution. These powdered, organic resin particles are readily dispersible in other resin media such as polyethylene. The pigments are very finely divided, usually 100 percent sub-sieve finer than 325 mesh (44 microns).

The matrix resin for the pigment particles is selected depending on the solubility and heat resistance required. For example, a polyamide matrix provides solvent resistance to a much wider variety of solvents than matrix resins based on sulphonamide, triazine and aldehyde. A representative commerical pigment is the Z series of Day-Glo fluorescent pigments which consist of a polyamide matrix containing fluorescent dye. These pigments have an average particle size of 10-12 microns, a specific gravity of 1.14, a softening point of 110°-115° C. and a decomposition point of 345° C. They are very compatible with polyethylene resins, especially high density polyethylene.

Referring now to FIG. 1, the taggant particles are prepared in an apparatus including a blender 10, extruder 12, mill or grinder 14, classifier 16 and mixer 18. Polyethylene pellets 20 and fluorescent pigment particles 22 are added to the blender 10. The blended mixture 24 is extruded in the extruder 12 into pellets 26. The pellets 26 are ground to a finer size in the grinder 14 and classified between the screens 16 to −35 mesh taggant particles 30. The taggant particles 30 are added to a construction material mixer 18 to form a coded material 32.

Figure 2:
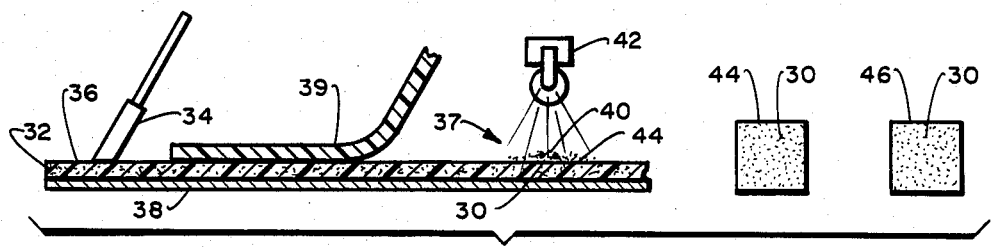
FIG. 2 is a schematic view of an identification system according to the invention.

Referring now to FIG. 2, a coded composition 32, such as an adhesive, is applied by a spreader 34 as a layer 36 on a substrate 38. A floor covering, such as a sheet 39 of tile or vinyl or other material, is installed over the adhesive layer 36. When it is necessary to determine the source of the adhesive layer 37, the sheet 39 is pulled away from the layer 36 and a sample 40 of the layer is exposed to an ultraviolet light from a source 42 which illuminates a pattern 44 of taggant particles 30. The pattern 44 can be visually compared to a standard 46 to determine the source of the adhesive.

The composition to be coded with taggant initially is in the form of a solution, dispersion of emulsion of resin or elastomer in a vaporizable liquid diluent or solvent. The resin can be laid down by evaporation to form a film or can be cured by air or catalyst after being applied to a substrate. The composition contains from 30 to 90 parts of resin, usually from 50 to 80 parts. The composition can also contain various other ingredients such as pigments, extenders, fillers, resin modification or curing agents, etc. The viscosity of composition can vary from thick as paste to a flowable liquid such as a paint. As little as one ounce of taggant particles per 100 gallons of composition is visible in the layers of the composition. Amounts over one pound per 100 gallons are not required and can cause excessive fluorescence. The taggant particles are insoluble in the liquid diluent and are inert thereto. The pellets may swell in the diluent as long as the dye is not leached from the particles. The diluent can be water, a petroleum distillate, aromatic hydrocarbon, a ketone such as methyl ethyl ketone or acetone.

The ease of discerning the taggant particles in dried films varies. The easiest situation is found in fairly hard films which fail cohesively when pulled apart. For example, typical carpet adhesive when the carpet is pulled up reveals a ruptured film with clean, uncoated taggant particles which are readily seen.

Where a somewhat gummy substance is involved, the taggant particles do not break clean and some scraping is necessary to make the taggants show up, even with "black light."

Films which are, themselves, fluorescent or films, such as asphalt which are gummy and opaque, can hide the taggants from easy view, even with scraping.

In these cases, the taggants can be extracted from the film with an appropriate heavy solvent. For example, a portion of dried film of taggant-bearing asphalt coating can be dissolved in trichloroethane. The taggants, having a lower density than the solvent, float to the surface. They are then readily seen with black light even though the solution is black.

In some attempts at solvent extraction, the taggants remained bound to insoluble organic material or mineral fillers and won't float to the surface. In these cases, it is merely necessary to filter out the residue. When dried, the residue readily reveals the taggants under black light. Any appropriate solvent can be used if filtration is employed since flotation of the taggant particles is not involved.

The taggants can be added to an almost limitless variety of adhesives and coatings including soluble, thermoplastic binders which remain soluble after removal of solvent or diluent or thermosetting binders which are insoluble after use. The latter materials can not be subjected to the extraction process previously discussed to free the particles for qualitative visual inspection. Exemplary products that can be coded are listed below:

| Roof Cements | Tile Adhesives: Ceramic, |
| Roof Coatings | Brick, Plastic and Acoustical Tiles |
| Special Purpose Coatings | Floor Covering Adhesives: |
| Construction Adhesives | Sheet goods, Tile and |
| Gypsum Drywall & Foam Insulation Adhesives | Carpet |

The invention will now be illustrated by a representative number of examples of practice. It is understood that the fluorescent taggants can readily be dispersed in any of the above-described resin-based compositions or other similar products.

EXAMPLE 1

Taggant Particles

Taggant particles were prepared by combining 3 percent by weight of Day-Glo Z-14 Fire Orange plastic grade fluorescent pigment (dyed polyamide) into high-density polyethylene in a blender, extruding into pellets and grinding and sieving to 35 mesh taggant particles.

One-half pound of the taggant particles were added to 100 gallons of the following products.

EXAMPLE 2

Latex Base Adhesive

|  | Weight % |
| --- | --- |
| Binder (styrene-butadiene synthetic rubber and hydrocarbon resins) | 30 |
| Mineral filler (clay) | 18 |
| Water | 52 |
|  | 100 |

EXAMPLE 3

Solvent Based Adhesive

|  | |
| --- | --- |
| Binder (styrene-butadiene synthetic rubber and hydrocarbon resins) | 30 |
| Mineral filler (clay and limestone) | 38 |
| Mixed hexanes | 32 |
|  | 100 |

EXAMPLE 4

Asphalt Compound

|  | |
| --- | --- |
| Air Blown Asphalt (140° F. softening point) | 63 |
| Asbestos fines (7R grade) | 5 |
| Petroleum Naphtha (250-280 B.P.) | 32 |
|  | 100 |

The taggant containing compositions of Examples 2–4 were spread onto a panel and allowed to dry. Some taggant particles were evident on the surface of two of the films (Examples 2 and 3) under U.V. light but scuffing the top surface of the film cleanly exposed many more taggant particles which fluoresced brilliantly under the light. The mineral filler tends to reduce the natural fluorescence of the binder resin and also reduces the adhesion of the resin to the taggant particles. In the third film (Example 4), the soft, sticky asphalt binder coats the taggant particles so effectively that even a skilled technician can barely discern the presence of taggants.

Sincer asphalt is soluble in solvent, however, the taggant can be extracted from the film.

EXAMPLE 5

A lump of film of Example 4, about the size of a bean, was dissolved in 1,1,1-trichloroethane. Clean taggant particles float to the surface. Under U.V. light the particles show up brilliantly, moving around on the solvent surface.

By pouring the entire contents through a paper filter and washing the residue with additional solvent still more taggant particles are exposed. This added procedure is also helpful in exposing taggants from compositions in which they become entangled in fillers or other insoluble matter.

It is to be realized that only preferred embodiments of the invention have been described and that numerous substitutions, modifications and alterations are permissible without departing from the spirit and scope of the invention as defined in the following claims.

We claim:

1. A film-forming, viscous composition comprising a liquid diluent containing from 30 to 90 parts by weight of a film-forming resin in which is dispersed solid, discrete fluorescent taggant particles in an amount from 0.1 oz. to 5 pounds per gallon of said composition, said particles being insoluble in the diluent and being formed of fluorescent dyed powder dispersed in a solid transparent plastic binder resin and being readily discernible when the film is exposed to ultraviolet light.

2. A composition according to claim 1 in which the composition is a construction material.

3. A composition according to claim 2 in which the composition is an adhesive, coating or sealant material.

4. A composition according to claim 1 in which the diluent is selected from water or an organic solvent.

5. A composition according to claim 4 in which the film-forming resin is a latex dispersed in water.

6. A composition according to claim 4 in which the film-forming resin remains soluble after removal of the diluent.

7. A composition according to claim 1 in which the powder consists essentially of a solution of fluorescent dye in a cured, condensation resin.

8. A composition according to claim 7 in which the condensation resin is selected from amine aldehyde or polyamide resins.

9. A composition according to claim 7 in which the particles are a −35 mesh.

10. A composition according to claim 9 in which the binder resin is a polyolefin.

11. A composition according to claim 10 in which the polyolefin is a high density polyethylene.

12. A method of coding a viscous, film-forming resin composition formed of a liquid diluent which contains 30 to 90 parts by weight of a film-forming resin comprising dispersing in said resin taggant particles which are hard, discrete, solid fluorescent particles insoluble in the diluent and being formed of fluorescent dyed powder dispersed in a solid, transparent binder resin and being readily discernible when the film is exposed to ultraviolet light.

13. A method according to claim 12 in which the diluent is selected from water or an organic solvent and the composition is a construction material selected from an adhesive, coating or sealant material.

14. A method according to claim 13 in which the film-forming resin is selected from a synthetic or natural elastomer or resin.

15. A method according to claim 13 in which the powder consists essentially of a fluorescent dyed, cured, condensation resin.

16. A method according to claim 12 further including the steps of applying a film of the composition to a substrate and removing diluent.

17. A method according to claim 16 further including the step of illuminating the film with ultraviolet light and observing the pattern of taggant particles.

18. A method according to claim 16 further including the step of dissolving a portion of the film in a solvent for the resin to free the taggant particles.

19. A method according to claim 18 in which the solvent is denser than the particles and further including the steps of floating the taggant particles to the surface of the solvent, illuminating the surface with ultraviolet light and observing the pattern of taggant particles.

20. A method according to claim 19 in which the denser solvent is 1,1,1-trichloroethane.

21. A method according to claim 18 further including the additional step of filtering out residue and subjecting the residue to additional washings with solvent to further expose taggants to illumination and fluorescence.

22. A composition according to claim 9 in which taggant particles contain less than 20 percent fines below 325 mesh.

23. A method according to claim 12 in which the taggant particles contain less than 20 percent fines below 325 mesh.

* * * * *